under

US010981814B2

(12) United States Patent
Waul et al.

(10) Patent No.: US 10,981,814 B2
(45) Date of Patent: Apr. 20, 2021

(54) CONTROL SYSTEM FOR OPTIMIZING MIXING AND ENERGY USAGE FOR MIXING SYSTEMS

(71) Applicant: Evoqua Water Technologies LLC, Pittsburgh, PA (US)

(72) Inventors: Christopher K. Waul, Waukesha, WI (US); Argun Olcayto Erdogan, Greenfield, WI (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 0 days.

(21) Appl. No.: 16/467,263

(22) PCT Filed: Dec. 8, 2017

(86) PCT No.: PCT/US2017/065239
§ 371 (c)(1),
(2) Date: Jun. 6, 2019

(87) PCT Pub. No.: WO2018/106986
PCT Pub. Date: Jun. 14, 2018

(65) Prior Publication Data
US 2020/0079667 A1 Mar. 12, 2020

Related U.S. Application Data

(60) Provisional application No. 62/432,145, filed on Dec. 9, 2016.

(51) Int. Cl.
*C02F 3/12* (2006.01)
*B01F 5/02* (2006.01)
(Continued)

(52) U.S. Cl.
CPC .......... *C02F 3/1284* (2013.01); *B01F 5/0206* (2013.01); *B01F 13/0222* (2013.01);
(Continued)

(58) Field of Classification Search
CPC .. C02F 3/1284; B01F 5/0206; B01F 13/0222; B01F 15/00175; B01F 15/0022
(Continued)

(56) References Cited

U.S. PATENT DOCUMENTS 4,787,987 A * 11/1988 Hensley ................. B01D 24/12
210/792
5,401,412 A    3/1995 Yang et al.
(Continued)

FOREIGN PATENT DOCUMENTS

CN        101700475 B     11/2012
SU          1157940 A1     1/1986
(Continued)

OTHER PUBLICATIONS

Lonneke, Mulder, "European Search Report", European Patent Application No. 17877597.9, dated Jun. 17, 2020, 8 pages.
(Continued)

*Primary Examiner* — Claire A Norris

(57) ABSTRACT

A method and system for treating wastewater is disclosed. In one example the method comprises activating a mixing system that imparts a motive force on wastewater in a vessel, measuring at least one property of a first portion of the wastewater at a first time, measuring the at least one property of a second portion of the wastewater at a second time subsequent to the first time, calculating a difference between the at least one property measured at the first time and the at least one property measured at the second time, performing a determination of whether the difference is within a predetermined allowable range of differences, and responsive to a result of the determination, controlling a component of the mixing system.

12 Claims, 9 Drawing Sheets

(51) Int. Cl.
  *B01F 13/02* (2006.01)
  *B01F 15/00* (2006.01)
(52) U.S. Cl.
  CPC .... *B01F 15/0022* (2013.01); *B01F 15/00175* (2013.01); *C02F 2209/02* (2013.01); *C02F 2209/04* (2013.01); *C02F 2209/06* (2013.01); *C02F 2209/10* (2013.01); *C02F 2209/22* (2013.01)
(58) Field of Classification Search
  USPC .......................................... 210/614, 739, 143
  See application file for complete search history.

(56) References Cited

U.S. PATENT DOCUMENTS

| | | | |
|---|---|---|---|
| 5,458,414 | A | 10/1995 | Crump et al. |
| 6,093,322 | A * | 7/2000 | Bongards ................ C02F 3/006 210/614 |
| 2008/0202216 | A1 | 8/2008 | Campbell et al. |
| 2008/0264843 | A1 | 10/2008 | Yamasaki et al. |
| 2009/0314695 | A1 * | 12/2009 | Lescoche ............... B01D 61/18 210/87 |
| 2010/0243558 | A1 * | 9/2010 | Ekster ................... C02F 3/2833 210/603 |
| 2012/0315209 | A1 | 12/2012 | Bisson et al. |
| 2013/0126440 | A1 * | 5/2013 | Prause ................. E04H 4/1209 210/743 |
| 2014/0138308 | A1 * | 5/2014 | Elger ..................... C02F 3/006 210/605 |
| 2015/0048026 | A1 * | 2/2015 | Jenkins .................. C02F 3/302 210/614 |
| 2016/0185616 | A1 | 6/2016 | Wright et al. |

FOREIGN PATENT DOCUMENTS

| | | |
|---|---|---|
| WO | 2013177632 | 12/2013 |
| WO | 2014152872 | 9/2014 |

OTHER PUBLICATIONS

Unknown, "Communication pursuant to Rules 70(2) and 70a(2) EPC", European Patent Application No. 17877597.9, dated Jul. 7, 2020, 1 page.

Unknown, First Office Action, Chinese Patent Application 201780075902.3, dated Jul. 3, 2020, 17 pages.

* cited by examiner

CONTROL SYSTEM FOR OPTIMIZING MIXING AND ENERGY USAGE FOR MIXING SYSTEMS

RELATED APPLICATIONS

This application is a U.S. national stage application and claims the benefit under 35 U.S.C. § 371 of PCT/US2017/065239, filed Dec. 18, 2017, titled "CONTROL SYSTEM FOR OPTIMIZING MIXING AND ENERGY USAGE FOR MIXING SYSTEMS," which claims priority to U.S. Provisional Application Ser. No. 62/432,145, titled "CONTROL SYSTEM FOR OPTIMIZING MIXING AND ENERGY USAGE FOR HYDRAULIC MIXING SYSTEMS," filed Dec. 9, 2016. Each of these applications is incorporated herein by reference in its entirety for all purposes.

BACKGROUND

Technical Field

The technical field relates generally to wastewater treatment systems, and more specifically to wastewater treatment systems that utilize mixing systems.

Background Discussion

Various methods for the treatment of wastewater involve mixing applications. For instance, liquid sludge may be stored in a storage tank over a period of time. The contents of the tank settle during this period, and a crust may form on the upper surface of the stored sludge material. The settled material typically has to be re-mixed before it can be pumped out of the tank. In other wastewater applications, the liquid sludge is continuously mixed to maintain the sludge solids in suspension. The costs associated with maintaining the sludge in a slurry form can be significant.

SUMMARY

Aspects and embodiments are directed to a method and system for treating wastewater that is configured to efficiently mix wastewater or sludge while minimizing energy consumption.

In accordance with an aspect of the present disclosure there is provided a method for treating wastewater. The method comprises activating a mixing system that imparts a motive force on wastewater in a vessel, measuring at least one property of a first portion of the wastewater at a first time, measuring the at least one property of a second portion of the wastewater at a second time subsequent to the first time, calculating a difference between the at least one property measured at the first time and the at least one property measured at the second time, performing a determination of whether the difference is within a predetermined allowable range of differences, and responsive to a result of the determination, controlling a component of the mixing system.

In accordance with some embodiments controlling the component includes deactivating the component responsive to the difference being within the predetermined allowable range of differences.

In accordance with some embodiments controlling the component includes one of modulating or maintaining power supplied to the component responsive to the difference being outside the predetermined allowable range of differences.

In accordance with some embodiments the method further comprises measuring the at least one property of the first portion of the wastewater while the first portion of the wastewater is inside the vessel, removing the second portion of the wastewater from the vessel, and measuring the at least one property of the second portion of the wastewater while the second portion of the wastewater is outside the vessel.

In accordance with some embodiments removing the second portion of the wastewater from the vessel includes introducing the second portion of the wastewater into a recirculation loop fluidly connected between an outlet of the vessel and an inlet of the vessel.

In accordance with some embodiments the method further comprises re-introducing the second portion of the wastewater to the vessel after measuring the at least one property of the second portion of the wastewater.

In accordance with some embodiments measuring the at least one property of the first portion of the wastewater includes measuring a property selected from the group consisting of temperature, pH, total suspended solids (TSS), dissolved oxygen (DO), and oxidation reduction potential (ORP).

In accordance with another aspect of the present disclosure there is provided a wastewater treatment system. The wastewater treatment system comprises a mixing system configured to impart a motive force on wastewater in a vessel, a plurality of sensors configured to measure at least one property of the wastewater, and a controller in communication with the plurality of sensors and a component of the mixing system. The controller is configured to activate the mixing system, obtain a first measured value for the at least one property at a first time using at least one sensor of the plurality of sensors subsequent to activating the mixing system, obtain a second measured value for the at least one property at a second time subsequent to the first time using at least one sensor of the plurality of sensors, calculate a difference between the first measured value and the second measured value, perform a comparison between the difference and a predetermined threshold, and responsive to a result of the comparison, control the component of the mixing system.

In accordance with some embodiments the mixing system is a hydraulic mixing system and the component is a motor driven pump positioned external to the vessel and fluidly connectable to an internal volume of the vessel via a supply conduit and a return conduit, the supply conduit fluidly connectable to a discharge side of the motor driven pump and the return conduit fluidly connectable to a suction side of the motor driven pump.

In accordance with some embodiments the hydraulic mixing system includes at least two nozzles fluidly coupled to the supply conduit and positioned within the vessel, and the motor driven pump is configured to withdraw wastewater from the vessel through the return conduit and to introduce wastewater to the vessel through the supply conduit and the at least two nozzles.

In accordance with some embodiments at least one sensor of the plurality of sensors is positioned at one of the supply conduit and the return conduit.

In accordance with some embodiments at least one sensor of the plurality of sensors is positioned within the internal volume of the vessel.

In accordance with some embodiments the at least two nozzles are configured to generate jet plumes of wastewater that sweep a bottom of the vessel and create a rotating toroidal flow pattern of the wastewater within the vessel.

In accordance with some embodiments the controller is configured to deactivate the motor driven pump responsive to the difference being within the predetermined threshold.

In accordance with some embodiments the controller is configured to one of modulate or maintain power supplied to the motor driven pump responsive to the difference exceeding the predetermined threshold.

In accordance with some embodiments the wastewater comprises activated sludge.

In accordance with some embodiments the vessel is configured as one of a digester and a sludge storage tank.

In accordance with some embodiments the at least one property is selected from the group consisting of temperature, pH, total suspended solids (TSS), dissolved oxygen (DO), and oxidation reduction potential (ORP).

In accordance with some embodiments the system further includes a sample loop having a portion positioned external to the vessel and fluidly connectable to an internal volume of the vessel, the sample loop configured to withdraw wastewater from the vessel and reintroduce the wastewater into the vessel.

In accordance with some embodiments at least one sensor of the plurality of sensors is positioned on the sample loop.

In accordance with some embodiments the mixing system is configured as a mechanical mixing system and the component is a motor driven mixing structure.

In accordance with some embodiments the motor driven mixing structure is one of an impeller, propeller, or plunger type linear motion device.

In accordance with some embodiments the mixing system is configured as a pneumatic mixing system and the component is a fluid control device fluidly coupled to a source of pressurized gas.

In accordance with some embodiments the pneumatic mixing system includes at least one diffuser nozzle positioned within the vessel and fluidly connectable to the source of pressurized gas.

In accordance with some embodiments the fluid control device is one of a valve and a motor driven pump.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
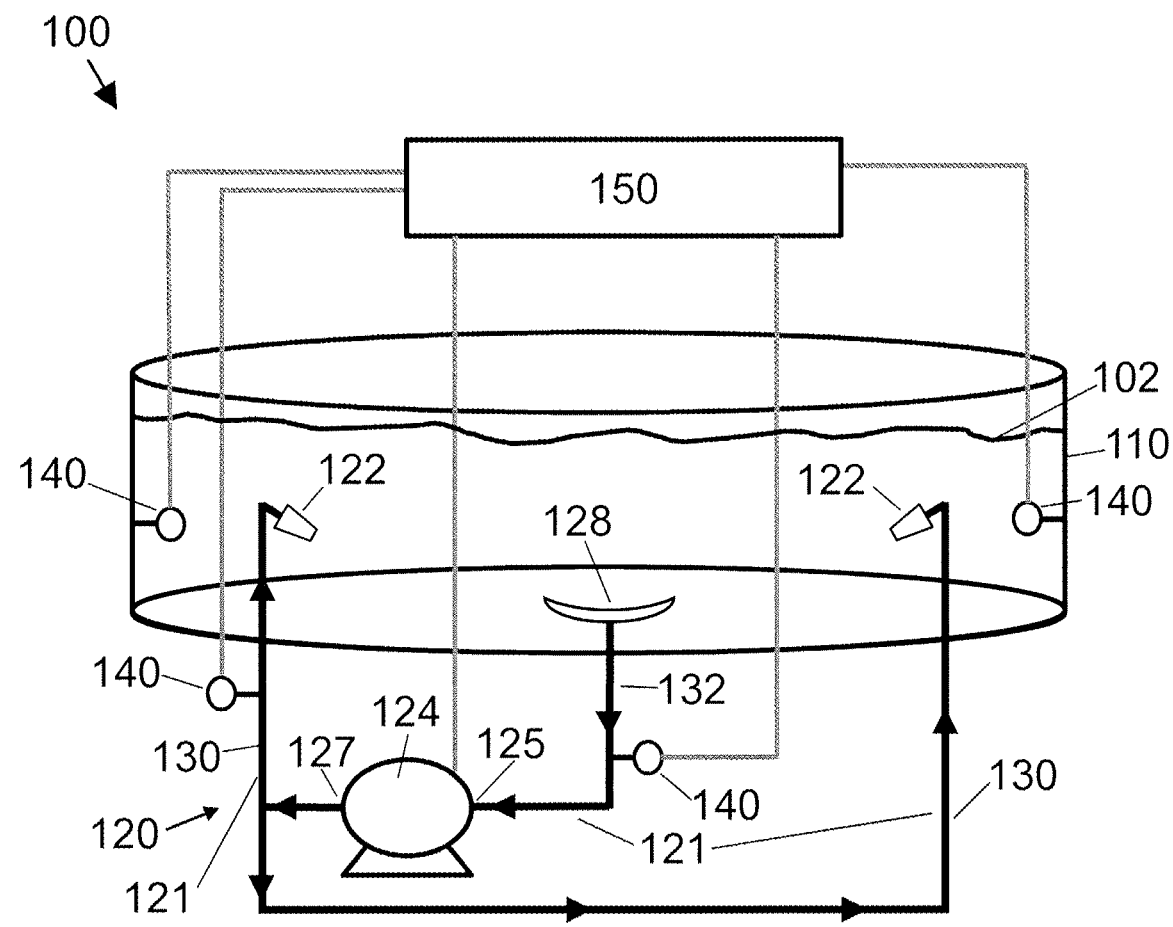
FIG. 1 is a schematic representation of one example of a wastewater treatment system that includes a hydraulic mixing system in accordance with one or more aspects of the invention.

Water is frequently used to transport unwanted waste materials to a treatment facility where the waste materials are either removed from or neutralized in the water. Wastewater treatment typically includes three general phases. The first phase, or primary treatment, involves mechanically separating dense solids from less dense solids and liquids in the wastewater. Primary treatment is typically performed in sedimentation tanks using gravity separation. The second phase, or secondary treatment, involves biological conversion of carbonaceous and nutrient material in the wastewater to more environmentally friendly forms. Secondary treatment is typically performed by promoting the consumption of the carbonaceous and nutrient material by bacteria and other types of beneficial organisms already present in the wastewater or that are mixed into the wastewater. The third phase, or tertiary treatment, involves removing the remaining pollutant material from the wastewater. Tertiary treatment is typically performed by filtration with the optional addition of chemicals, UV light, and/or ozone to neutralize harmful organisms and remove any remaining pollutant material.

One or more of the primary, secondary, and tertiary treatment processes may involve mixing at some point in the process. For example, mixing may be performed in long-term sludge storage tanks, in anaerobic and aerobic digesters, leachate, backwash, blend, and flow equalization tanks, and in anoxic zones of treatment vessels. Other waste applications, such as agricultural, food processing, pulp and paper, and mining waste, and fertigation systems may also involve mixing operations.

Conventional mixing systems are configured to operate on either a continuous or clock timer basis. This types of operations are costly due to the large amounts of energy that are involved and may also cause other problems, such as over-mixing, which can cause foaming, or under-mixing which reduces process performance. Aspects and embodiments of the disclosed system and process are configured to reduce energy consumption while maintaining optimum process performance, for example, optimum volatile solids destruction.

In accordance with one or more embodiments, the methods and systems described herein relate to treating wastewater. One or more embodiments pertinent to some aspects of the invention can involve methods and techniques of treating wastewater that comprise activating a mixing system that imparts a motive force on wastewater in a vessel. The motive force causes fluid flow of wastewater in the vessel. The mixing system may be configured as one of a hydraulic, mechanical, or pneumatic mixing system for invoking the motive force, as characterized and discussed below.

The wastewater may contain waste matter which, in some instances, can comprise solids and soluble and insoluble organic and inorganic material. As used herein, the terms "water," "wastewater," and "wastewater stream" can refer to water to be treated such as streams or bodies of water from residential, commercial, or municipal, industrial, and agricultural sources, as well as mixtures thereof, that typically contain at least one undesirable species, or pollutant, comprised of biodegradable inorganic or organic materials which can be decomposed or converted by biological processes into environmentally benign or at least less objectionable compounds. The water to be treated can also contain biological solids, inert materials, organic compounds, including recalcitrant or a class of compounds that are difficult to biodegrade relative to other organic compounds as well as constituents from ancillary treatment operations such as, but not limited to, nitrosamines and endocrine disruptors.

In accordance with at least one embodiment, the wastewater comprises components having different densities or specific gravities. For instance, the wastewater may comprise solids or semi-solids and liquid, such as biomass and water. In some embodiments, the wastewater may comprise solid particulates or suspended solids in a liquid. In one embodiment, the wastewater is a slurry comprising solid and liquid components. According to certain embodiments, the wastewater may include wastewater from any one of a primary, secondary, or tertiary wastewater treatment process. For example, the wastewater may comprise activated sludge. According to at least one embodiment, the wastewater comprises different phases, such as an organic phase and an aqueous phase.

In certain embodiments, the wastewater may comprise activated sludge, and the vessel used for the treatment process may be configured as one of a digester or a sludge storage tank. For example, the vessel may be configured as an anaerobic or aerobic digester. According to certain embodiments, mixing provided by a mixing system in a treatment process may mix the wastewater for purposes of placing or maintaining sludge solids in suspension.

The methods and techniques of the invention may further comprise measuring at least one property of a first portion of the wastewater at a first time, and measuring the at least one property of a second portion of the wastewater at a second time subsequent to the first time. The at least one property may be any chemical, physical, or biological property of the wastewater that may be used to monitor and/or control a wastewater treatment process. Non-limiting examples of such properties include conductivity, temperature, pH, and concentration or levels of total suspended solids (TSS), volatile suspended solids (VSS), dissolved oxygen (DO), oxidation reduction potential (ORP), nitrate ($NO_3^-$), nitrite ($NO_2^-$), ammonia ($NH_3$), ammonium ($NH_4^+$), total nitrogen (TN), orthophosphate ($PO_4^{3-}$), and/or total phosphorous (TP).

The methods and techniques of the invention may further comprise calculating a difference between the at least one property measured at the first time and the at least one property measured at the second time, performing a determination of whether the difference is within a predetermined allowable range of differences or predetermined threshold, and responsive to a result of the determination, controlling a component of the mixing system. For example, according to some embodiments, controlling the component may include deactivating the component responsive to the difference being within the predetermined allowable range of differences. According to other embodiments, controlling the component includes one of modulating or maintaining power supplied to the component responsive to the difference being outside the predetermined allowable range of differences. In accordance with certain embodiments, the predetermined allowable range of differences reflects wastewater that is mixed to a degree within the vessel sufficient to fulfill a process requirement. In some embodiments, the predetermined allowable range of differences reflects wastewater that is uniformly mixed or mixed to an acceptable degree within the vessel.

The various systems and techniques that use the control scheme for mixing disclosed herein can significantly reduce energy consumption compared to systems that use continuous or timed control schemes to control mixing. For instance, power may be supplied to components of a mixing system, such as a motor, only when successive measurements indicate that the wastewater has not been or is not adequately mixed. Successive measurements that are close in value indicate that the wastewater in the vessel has reached a steady state value or is otherwise not changing, and therefore components of the mixing system, such as the motor, may be powered off. Thus, mixing is provided only when it is desired to fulfill a process requirement. Furthermore, problems associated with over- and under-mixing can be avoided, such as foaming or reduced bacterial degradation rates. According to various aspects, the control scheme disclosed herein can reduce power consumption by at least 50%, and in some instances reduce power consumption by at least 75%, when compared to a conventional control scheme, such as a control scheme configured to operate a mixing system on a continuous basis.

In further embodiments of the invention, methods and techniques can comprise measuring the at least one property of the first portion of the wastewater while the first portion of the wastewater is inside the vessel. The methods and techniques can also comprise removing the second portion of the wastewater from the vessel and measuring the at least one property of the second portion of the wastewater while the second portion of the wastewater is outside the vessel. According to at least one embodiment, removing the second portion of the wastewater from the vessel includes introducing the second portion of the wastewater into a recirculation loop fluidly connected between an outlet of the vessel and an inlet of the vessel. According to some embodiments, the methods and techniques further comprise re-introducing the second portion of the wastewater to the vessel after measuring the at least one property.

One or more embodiments pertinent to some aspects of the invention can involve a wastewater treatment system comprising a mixing system configured to impart a motive force on wastewater in a vessel, a plurality of sensors configured to measure at least one property of the wastewater, and a controller in communication with the plurality of sensors and at least one component of the mixing system. The at least one property of the wastewater that is measured by a sensor of the plurality of sensors may be any one of the properties previously discussed, such as temperature, pH, TSS, DO, and/or ORP. According to certain embodiments, the controller may be configured to activate the mixing system and to obtain a first measured value for the at least one property at a first time using at least one sensor of the plurality of sensors. In some embodiments, the first measured value is obtained subsequent to activating the mixing system. The controller may also be configured to obtain a second measured value for the at least one property at a second time subsequent to the first time using at least one sensor of the plurality of sensors, calculate a difference between the first measured value and the second measured value, perform a comparison between the difference and a predetermined threshold, and responsive to a result of the comparison, control the component of the mixing system.

According to certain embodiments, the first measured value is obtained from at least one sensor positioned within an internal volume of the vessel, and the second measured value is obtained from at least one sensor positioned external to the vessel. For example, the first measured value(s) may be made by one or more sensors positioned at various locations within the internal volume of the vessel, and the second measured value may be obtained by one or more sensors positioned external to the vessel, such as at or within a recirculation or sample loop.

In further embodiments of the invention, the mixing system is configured as a hydraulic mixing system, and the component of the hydraulic mixing system that is controlled by the controller is a motor driven pump positioned external to the vessel and fluidly connected or connectable to an internal volume of the vessel via a supply conduit and a return conduit. According to some embodiments, the supply conduit is fluidly connected or connectable to a discharge side of the motor driven pump and the return conduit is fluidly connected or connectable to a suction side of the motor driven pump. In one embodiment, the hydraulic mixing system includes at least two nozzles fluidly coupled to the supply conduit and positioned within the vessel. The motor driven pump may be configured to withdraw wastewater from the vessel through the return conduit and to introduce wastewater to the vessel through the supply conduit and the at least two nozzles. According to a further embodiment, at least one sensor may be positioned at or within one of the supply conduit and the return conduit.

According to some embodiments of the invention, the system can comprise a sample loop having a portion positioned external to the vessel and fluidly connected or connectable to an internal volume of the vessel. The sample loop may be configured to withdraw wastewater from the vessel and reintroduce the wastewater into the vessel. In one embodiment, at least one sensor is positioned on or within the sample loop.

In other embodiments of the invention, the mixing system is configured as a mechanical mixing system, and the component of the mechanical mixing system that is controlled by the controller is a motor driven mixing structure. In one embodiment, the motor driven mixing structure is one of an impeller, propeller, paddle wheel, or a plunger type linear motion device.

In still other embodiments of the invention, the mixing system is configured as a pneumatic mixing system, and the component of the pneumatic mixing system that is controlled by the controller is a fluid control device fluidly coupled to a source of pressurized gas. In some embodiments, the fluid control device is one of a valve and a motor driven pump. According to one embodiment, the pneumatic mixing system comprises at least one diffuser nozzle. The at least one diffuser nozzle of the pneumatic mixing system may be positioned within the vessel and fluidly connected or connectable to the source of pressured gas.

A schematic of a wastewater treatment system according to one embodiment is shown generally at 100 in FIG. 1. The system 100 includes a tank or vessel 110, a mixing system 120, at least one sensor 140, and a controller 150.

The vessel 110 functions as a containment unit for wastewater 102. As used herein, the terms "vessel" and "tank" are used interchangeably and broadly refer any structure suitable for confining one or more process components, including gas, liquid, and solid components and mixture thereof. The vessel 110 may be open to the environment, or may be closed, and may be sized and shaped according to a desired application and volume of wastewater to be stored and/or or treated. According to some embodiments, the vessel 110 is cylindrical in shape, but in alternative embodiments, the vessel may have sidewalls with multiple, non-continuous side portions, such as an octagon or hexagon. The vessel 110 may be constructed of any material suitable for the purposes of the methods and systems described herein. Non-limiting examples of suitable materials include steel, including stainless steel, fiberglass reinforced plastic, polyvinyl chloride (PVC), concrete, and in some instances, porcelain coated steel. The floor of the vessel 110 may be flat and horizontal or of a slightly conical configuration with the tip of the cone pointing either upward or downward.

Wastewater 102 present in vessel 110 may be any wastewater as previously described. For instance, the wastewater 102 may be activated sludge.

The mixing system 120 is configured to impart a motive force on the wastewater 102 in the vessel 110. According to some embodiments, the mixing system 120 is configured as a hydraulic mixing system. As used herein, the term "hydraulic mixing" refers to imparting a motive force on wastewater in the vessel via hydraulic energy, and certain instances refers to imparting motive force on wastewater in the vessel using a fluid. As described in further detail below, the fluid used by the hydraulic mixing system 120 may be wastewater 102 from the vessel 110.

The hydraulic mixing system 120 of system 100 includes at least two nozzles 122 or other fluid flow generating devices positioned within the vessel 110. The at least two nozzles 122 may be submerged within the wastewater 102 present in the vessel 110, and in some embodiments, may be mounted to the floor of the vessel 110. In instances where the nozzles 122 are mounted to the floor of the vessel 110, piping to the nozzles may be located underneath the floor of the vessel. The number of nozzles 122 used may depend on a number of factors, including the size of the tank and the particular application. For instance, the number of nozzles may depend on the surface area of the floor of the vessel.

According to various aspects, the nozzles 122 may be configured to provide a discharge velocity for the wastewater of about 35-40 feet per second (fps, 10.7 m/s-12.2 m/s) discharge velocity (based on water as the discharge fluid). In some embodiments, the nozzles 122 are configured to provide a discharge velocity of at least 25 fps (7.6 m/s). Discharge velocities that exceed 40 fps (12.2 m/s) are also within the scope of this disclosure.

In accordance with certain embodiments, the at least two nozzles 122 are configured to generate jet plumes of wastewater 102 that sweep a bottom of the vessel 110 and create a rotating toroidal flow pattern of the wastewater within the vessel 110. The pattern may also include a helical flow pattern of the wastewater within the vessel that follows the surface of the toroid, rises along the vessel wall, and descends into the middle of the vessel 110 to effectively sweep solids from the center of the vessel 110.

Figure 5:
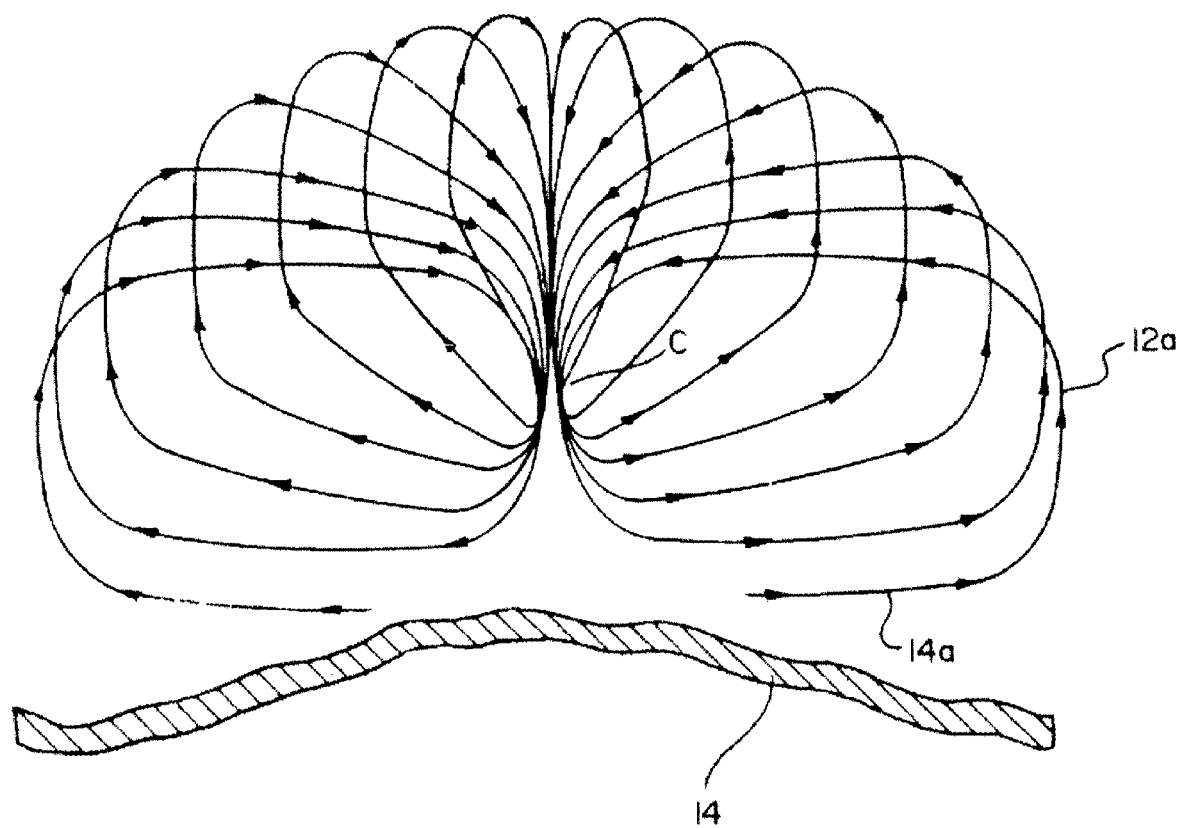
FIG. 5 is a schematic representation of a flow pattern within a vessel.

An example of such a flow pattern is shown in FIG. 5, and is described in U.S. Pat. No. 5,458,414 (herein referred to as the '414 patent), which is incorporated herein by reference. As described in the '414 patent, flow is directed along an outside wall of the vessel, across a surface of the wastewater present in the vessel, and downwardly along the vessel center C. The flow then sweeps across the vessel floor 14, including the point where the vertical center line C intersects the vessel floor 14. As indicated in FIG. 5, the flow pattern is also substantially helical, sweeping out an annular volume having a negligible center radius and an outer radius corresponding to that of the vessel wall. The flow lines shown in FIG. 5 include flow components 14a travelling across the vessel floor 14, and flow components 12a sweeping along the vessel wall, and returning downwardly at the center C of the vessel. This flow pattern creates an intensive mixing at the center of the vessel by creating a vortex-like characteristic therein. According to some embodiments, more than two nozzles may be used, and the number of nozzles may vary according to the size of the vessel, the physical properties of the wastewater 102, and the desired mixing flow pattern.

According to certain embodiments, each nozzle 122 is positioned at a radial distance of about 25% to about 75% from a center of the vessel 110. In further embodiments, each nozzle is positioned at a radial distance about 30% to about 70% from the center of the vessel 110. In some embodiments, the at least two nozzles 122 may be positioned along a common "ring" at the radial distance from the center of the vessel. Multiple "rings" of nozzles may be used within the vessel. Each nozzle 122 may be configured to discharge wastewater away from the tank center. According to certain aspects each nozzle 122 may be operated through an acute angle ranging between 0 degrees and 60 degrees as measured from a line perpendicular to a radius from the center of the vessel, and extending through the nozzle 122. The nozzles 122 may be angled slightly outwardly away from the center of the vessel. In some embodiments, the nozzles 122 are configured to discharge wastewater at an angle of between 3 degrees and about 7 degrees below horizontal. In some embodiments, the nozzles 122 are configured to discharge wastewater at an angle of 5 degrees below horizontal. The size of the diameter or discharge orifice of the nozzles 122 may vary according to the particular implementation. In one embodiment, orifices of the nozzles 122 have a diameter of 6 inches, although it is to be appreciated that the geometry of the nozzle may depend on any one of a number of different factors, including the flow rate, tank geometry, and the particular application. In another embodiment, the nozzles 122 include flow control vanes to reduce turbulence. The nozzles 122 in the vessel 110 may each be directed in a similar manner, and may be directed in a clockwise direction.

The wastewater treatment system 100 also includes at least one sensor 140 that is configured to measure at least one property of the wastewater 102. In some embodiments, a plurality of sensors may be used, and in other embodiments a single sensor may be used. The sensor 140 may measure one or more properties of the wastewater 102, including one or more of the properties previously discussed, such as the temperature, pH, TSS, DO, and/or ORP of the wastewater 102. The sensor(s) 140 may be in fluid communication with the wastewater 102 for purposes of taking measurements. According to the embodiment shown in FIG. 1, at least one sensor 140 is positioned external to the vessel 110, and at least one sensor is positioned within the vessel 110. In alternative embodiments, one or more sensors 140 may be positioned only external to the vessel 110, or only internal to the vessel 110. The sensor(s) 140 may be configured to be controlled by the controller 150, and may be capable of receiving an input signal from the controller 150 that instructs the sensor(s) 140 to take a measurement. The sensor(s) 140 may also be configured to send or otherwise transmit an output signal containing an indication of the measured property value back to the controller 150. As described herein, the controller 150 may use the measured value to control one or more components of the mixing system 120. In some embodiments, at least one sensor 140 may be configured to measure one or more properties of the wastewater 102 on a continuous basis. For instance, the controller 150 may instruct the at least one sensor 140 to measure continuously and send the measured values back to the controller 150. In some embodiments, sensors 140 positioned within the internal volume of the vessel 110 may be configured to measure on a continuous basis. In other embodiments, sensors 140 positioned both internal and external to the vessel 110 may be configured to measure on a continuous basis.

According to other embodiments, one or more sensors may be configured to measure an operating condition or parameter of the wastewater treatment system 100, such as a flow rate, pressure, or fluid level in the vessel 110. These measurements may also be used by the controller 150 to control one or more components of the wastewater treatment system. For instance, the controller 150 may activate a pump and/or valve to direct wastewater 102 into or out of the vessel 110 based on the level of wastewater (i.e., fluid level) present in the vessel.

In certain embodiments multiple vessels may be controlled by a single controller 150. The vessels may be configured to perform the same wastewater operation (e.g., digestion), or may be configured to perform operations in series, such that the contents of one vessel are transferred to another vessel during a larger process.

The hydraulic mixing system 120 of system 100 in FIG. 1 also includes a motor driven pump 124 that is positioned external to the vessel 110. The motor driven pump 124, which may also be referred to herein as a mixing pump, may be controlled by the controller 150 based on measurements taken by the sensor(s) 140. The motor driven pump 124 may be driven by electric or fuel power, and may be sized based on the size of the vessel 110, the desired flow rate, and the type of wastewater 102 being pumped. In accordance with one embodiment, the motor driven pump 124 may be any one of a centrifugal, positive displacement, or progressive cavity type of pump. According to certain embodiments, the motor driven pump 124 may be a chopper pump. In one embodiment, the motor driven pump 124 is a chopper pump that uses a centrifugal chopper impeller.

The hydraulic mixing system 120 also includes a supply conduit 130 that is fluidly connected or connectable to the at least two nozzles 122 and a discharge side 127 of the motor driven pump 124. A return conduit 132 of the hydraulic mixing system 120 is fluidly connected or connectable to a return inlet 128 and a suction side 125 of the motor driven pump 124. The motor driven pump 124 is fluidly connected or connectable to an internal volume of the vessel via the supply conduit 130 and the return conduit 132. According to certain embodiments, the return inlet 128 is positioned in the center the vessel 110. In some embodiments, the return inlet 128 may be positioned within the floor of the vessel 110, but in other embodiments the return inlet 128 may be positioned above the floor of the vessel 110. According to alternative embodiments, multiple return inlets may be used within the vessel.

The at least two nozzles 122 are fluidly coupled to the supply conduit 130, and the motor driven pump 124 is configured to withdraw wastewater 102 from the vessel 110 through the return inlet 128 and the return conduit 132 and the suction side 125 of the pump 124 and introduce wastewater to the vessel 110 through the discharge side 127 of the pump 124, the supply conduit 130, and the at least two nozzles 122. This flow pattern creates a closed loop that forms a recirculation loop 121 where the motor driven pump 124 removes a first portion of wastewater 102 from the vessel through an outlet of the vessel (i.e., return inlet 128) into the recirculation loop 121 and re-introduces the first portion of the wastewater 102 to the vessel through an inlet of the vessel (i.e., the at least two nozzles 122). The recirculation loop 121 is thereby fluidly connected between an outlet and inlet of the vessel, and a portion of the wastewater 102 may be introduced to the recirculation loop 102 for purposes of generating a hydraulic mixing effect in the vessel 110.

One example of a suitable hydraulic mixing system that may be used in embodiments of the disclosed invention is the Jetmix™ vortex mixing system available from Evoqua Water Technologies LLC (Warrendale, Pa.).

According to some embodiments, at least one sensor 140 is positioned within the internal volume of the vessel 110, and at least one sensor 140 is positioned external to the vessel 110. In some embodiments, multiple sensors 140 may be positioned within the internal volume of the vessel 110. Sensors 140 may be positioned at various locations within the vessel 110 for purposes of measuring one or more properties of wastewater 102 present in the vessel 110 at the various locations. At least one property of the wastewater 102 may thus be measured by the sensor(s) 140 while it is inside the vessel 110. In certain embodiments, at least one sensor 140 is positioned external to the vessel, such as at or in one of the supply conduit 130 and the return conduit 132, although in alternative embodiments, a sensor may be positioned at or in each of the supply and return conduits. At least one property of the wastewater 102 from the vessel 110 may thus be measured by the sensor(s) 140 while it is outside the vessel 110. Placing or otherwise locating the at least one sensor 140 external to the vessel 110 may provide one or more advantages, such as by allowing for easier access to the sensor(s) 140 for installation, replacement, maintenance, and/or calibration purposes.

The wastewater treatment system 100 also includes a controller 150 that is in communication or otherwise operatively coupled to the plurality of sensors 140 and at least one component of the mixing system 120. The controller 150 may be a single control unit or may include several control units. The sensor 140 is configured to transmit to the controller 150 the at least one measured value for the at least one property of the wastewater. The controller 150, can, based on the signals received from the at least one sensor 140, generate and send control signals to at least one component of the mixing system 120, and in some instances, may generate and send control signals to any of the components of the wastewater treatment system 100, such as valves and pumps. According to various aspects, the controller 150 may function to facilitate or regulate operating parameters of the wastewater treatment system.

According to at least one embodiment, the controller 150 is configured to activate the mixing system 120. In accordance with one embodiment, activating the mixing system 120 has the effect of mixing wastewater within the vessel 110. For example, in one embodiment, the controller 150 is configured to control power to the motor driven pump 124 such that the pump starts and begins pumping wastewater 102 from the vessel 110 via the return inlet 128, and re-introducing the wastewater 102 to the vessel 110 via the at least two nozzles 122. The controller 150 may initially activate the mixing system 120 based on an input signal, such as from a user or other control signal or device. For instance, if the vessel 110 is configured as a sludge storage tank, the contents may need to be mixed prior to removing them from the tank.

Once activated, the mixing system 120 mixes the wastewater 102 present in the vessel 110. The controller 150 may then use at least one sensor 140 to obtain a first measured value at a first time for at least one property of wastewater. In certain embodiments, the first measured value is obtained from at least one sensor 140 positioned within the interior volume of the vessel 110. The controller 150 may repeat the measurement at a second, later time, on wastewater removed from the vessel 110 that is present in the supply conduit 130 or return conduit 132, depending on the location of the sensor 140. For example, the controller 150 may use the at least one sensor 140 to obtain a second measured value at a second time for the at least one property of wastewater removed from the vessel 110. In some embodiments, the first measured value is obtained from a first portion of the wastewater 102 present in the vessel, and a second portion of the wastewater 102 is removed from the vessel 110 and one or more properties of the second portion of the wastewater is measured at the second time. The second portion is then re-introduced to the vessel 110 after the second measured value is obtained.

The controller 150 may then calculate a difference between the first measured value and the second measured value, and then perform a comparison between the difference and a predetermined threshold or predetermined allowable range of differences, and responsive to a result of the comparison, control a component of the mixing system 120. The controller 150 may therefore respond to the comparison result by generating a control signal that controls a component of the mixing system 120. For instance, when the comparison result indicates that the difference between the first measured value and the second measured value is within the predetermined threshold or predetermined allowable range of differences, this may indicate that the wastewater 102 in the vessel 110 is mixed to a degree sufficient to fulfill one or more process requirements and/or may reflect wastewater 102 that is uniformly mixed. The controller 150 may then deactivate the mixing system 120, for instance, by powering off the motor driven pump 124. In other instances, when the comparison result indicates that the difference is outside or exceeds the predetermined threshold or predetermined allowable range of differences, this may indicate the wastewater 102 in the vessel 110 is not mixed to a degree sufficient to fulfill the one or more process requirements and/or may reflect wastewater that is not uniformly mixed. In this case, the controller 150 may then modulate or maintain power supplied to the mixing system 120, such as the motor driven pump 124. For example, power may be maintained to the motor driven pump 124 and mixing of the wastewater 102 may thus be maintained within the vessel 110. In another example, the motor driven pump 124 may include a variable speed drive (VSD) or variable frequency drive (VFD) that allows power to the motor driven pump 124 to be modulated. For instance, power to the pump may be increased to increase the flow rate through the pump and thereby cause a stronger or greater motive force to act on the mixing flow pattern of wastewater in the vessel. In other embodiments, power to the pump may be decreased to decrease the flow rate through the pump, which lowers the motive force acting on the wastewater.

The amount of time that passes between when the first value of the at least one property of the wastewater is measured and the second value is measured may depend on one or more factors, such as the type of application, the size of the vessel, and the property being measured. In some embodiments, this value may be set by a user, such as a wastewater technician, and may be several seconds, minutes, or even hours.

In certain embodiments, the amount of time that passes between when the first measured value of the at least one property of the wastewater is measured and the second value is measured may be at least partially dependent on the turnover rate for the vessel 110. The vessel turnover rate may be calculated using the sum of the pump flow and the induced flow divided by the effective liquid volume of the tank. The plume flow is generated by the high velocity flow from the jet nozzle which generates a plume impacting the mixing in both the horizontal and vertical planes. The approximate plume flow calculated is generated from the anticipated plume geometry multiplied by the average plume velocity in the tank. A longer plume length may result in a higher turnover rate, and thus a more uniform distribution of energy. The mixing pattern has an effect on the plume development as well as the turnover rate.

In some embodiments, the turnover rate can be calculated according to the following formula:

Turnover rate (min)=Tank Volume (Gal)/(Nozzle Flow+Nozzle Plume Flow) $X$ #Nozzles According to some embodiments, the motor driven pump 124 may be activated by the controller 150 to operate at a predetermined time interval, for a predetermined period of time. According to one embodiment, predetermined time interval may be once every 60 minutes (i.e., once every hour), but in other embodiments, the predetermined time interval may be less than 60 minutes, e.g., 30 minutes or 45 minutes, or the predetermined time interval may be longer than 60 minutes, e.g., 90 minutes or 180 minutes. In one embodiment, the predetermined period of time may be 5 minutes, but in alternative embodiments, the time period may be shorter than 5 minutes, e.g., 2 minutes or 3 minutes, or may be longer than 5 minutes, e.g., 8 minutes, 10 minutes, 15 minutes, etc. According to some embodiments, the first value for the measured property of the wastewater 102 is measured by one or more sensors 140 positioned within the vessel 110, and the second value for the measured property of the wastewater 102 is measured by one or more sensors positioned external to the vessel 110. According to one embodiment, the first and second measurement values may be obtained during the time the motor driven pump 124 is operating in the same time interval. According to another embodiment, the second measurement value is obtained during the time the motor driven pump 124 is operating, but the first measurement value is from measurements taken within the vessel from the previous time interval (that the motor driven pump 124 was operating). If the difference between the first and second measured values is within the predetermined threshold, then the motor driven pump 124 can be controlled to deactivate after the predetermined period of time has expired (e.g., after 5 minutes). If the difference between the first and second measured values exceeds the predetermined threshold, then the motor driven pump 124 is controlled to continue to operate after the predetermined period of time has expired. According to some embodiments, measurements are obtained by a plurality of sensors 140 positioned within the vessel 110 at the first time and compared to the measured value at the second time, and the motor driven pump 124 is operated until all the comparison between each measurement taken within the vessel is within the predetermined threshold.

The values set for the predetermined threshold or predetermined allowable range of differences may also depend on one or more factors, including the type of operating value being measured, the application, and the size of the system. For instance, according to one embodiment, when temperature is included as a measured property of the wastewater, the predetermined threshold for the comparison result may be $\pm 1°$ F. or $\pm 1°$ C., meaning that if the difference between the first and second measured value is within $\pm 1°$ F. (or $\pm 1°$ C.), then the wastewater 102 in the vessel 110 is adequately mixed.

In accordance with some embodiments, the predetermined threshold or predetermined allowable range of differences may be based on a standard deviation or a statistical technique, such as a standard statistical process control (SPC) technique. For instance, in some embodiments statistical methods may be used to generate the predetermined threshold or allowable range of differences.

The control scheme used by the controller 150 in controlling the mixing system 120 allows for the controller 150 to use the measured property values while the motor driven pump 124 is running and continuously optimize the runtime of the pump. The control scheme allows for the pump to be stopped if the measured property values are not changing over time within a certain range, which indicates that the contents of the tank are uniformly mixed. However, if the difference between measured property values varies outside the predetermined range, or exceeds a predetermined threshold, then this indicates that the contents of the tank may require further mixing, and power to the pump may continue to be provided.

The controller 150 may be implemented using one or more computer systems which may be, for example, a general-purpose computer such as those based on an Intel® CORE™-type processor, a Motorola PowerPC® processor, a Hewlett-Packard PA-RISC® processor, a Sun Ultra-SPARC® processor, or any other type of processor or combination thereof. Alternatively, the computer system may include specially-programmed, special-purpose hardware, for example, an application-specific integrated circuit (ASIC) or controllers intended for water treatment systems.

The computer system can include one or more processors typically connected to one or more memory devices, which can comprise, for example, any one or more of a disk drive memory, a flash memory device, a RAM memory device, or other device for storing data. The memory may be used for storing programs and data during operation of the system. For example, the memory may be used for storing historical data relating to the parameters over a period of time, as well as operating data. Software, including programming code that implements embodiments of the invention, can be stored on a computer readable and/or writeable nonvolatile recording medium, and then copied into memory wherein it can then be executed by one or more processors. Such programming code may be written in any of a plurality of programming languages, for example, Java, Visual Basic, C, C#, or C++, Fortran, Pascal, Eiffel, Basic, or any of a variety of combinations thereof.

Components of the computer system may be coupled by one or more interconnection mechanisms, which may include one or more busses, e.g., between components that are integrated within a same device, and/or a network, e.g., between components that reside on separate discrete devices. The interconnection mechanism may enable communications, e.g., data and/or instructions, to be exchanged between components of the system.

The computer system can also include one or more input devices, for example, a keyboard, mouse, trackball, microphone, touch screen, and other man-machine interface devices as well as one or more output devices, for example, a printing device, display screen, or speaker. In addition, the computer system may contain one or more interfaces that can connect the computer system to a communication network, in addition or as an alternative to the network that may be formed by one or more of the components of the system.

According to one or more embodiments of the invention, the one or more input devices may include the previously described sensors 140 for measuring any one or more parameters of any of the systems disclosed herein and/or components thereof. Alternatively, the sensors, and/or other components of the system, such as valves and pumps, may all be connected to a communication network that is operatively coupled to the computer system. Any one or more of the above may be coupled to another computer system or component to communicate with the computer system over one or more communication networks. Such a configuration permits any sensor or signal-generating device to be located at a significant distance from the computer system and/or allow any sensor to be located at a significant distance from any subsystem and/or the controller, while still providing data therebetween. Such communication mechanisms may be affected by utilizing any suitable technique including but not limited to those utilizing wireless protocols.

The controller 150 can include one or more computer storage media such as readable and/or writeable nonvolatile recording medium in which signals can be stored that define a program to be executed by one or more processors. The medium may, for example, be a disk or flash memory. In typical operation, the one or more processors can cause data, such as code that implements one or more embodiments of the invention, to be read from the storage medium into a memory that allows for faster access to the information by the one or more processors than does medium.

Although the computer system is described by way of example as one type of computer system upon which various aspects of the invention may be practiced, it should be appreciated that the invention is not limited to being implemented in software, or on the computer system as exemplarily shown. Indeed, rather than implemented on, for example, a general purpose computer system, the controller, or components or subsections thereof, may alternatively be implemented as a dedicated system or as a dedicated programmable logic controller (PLC) or in a distributed control system. Further, it should be appreciated that one or more features or aspects of the invention may be implemented in software, hardware or firmware, or any combination thereof. For example, one or more segments of an algorithm executable by the controller 150 can be performed in separate computers, which can be in communication with one another through one or more networks.

Figure 2:
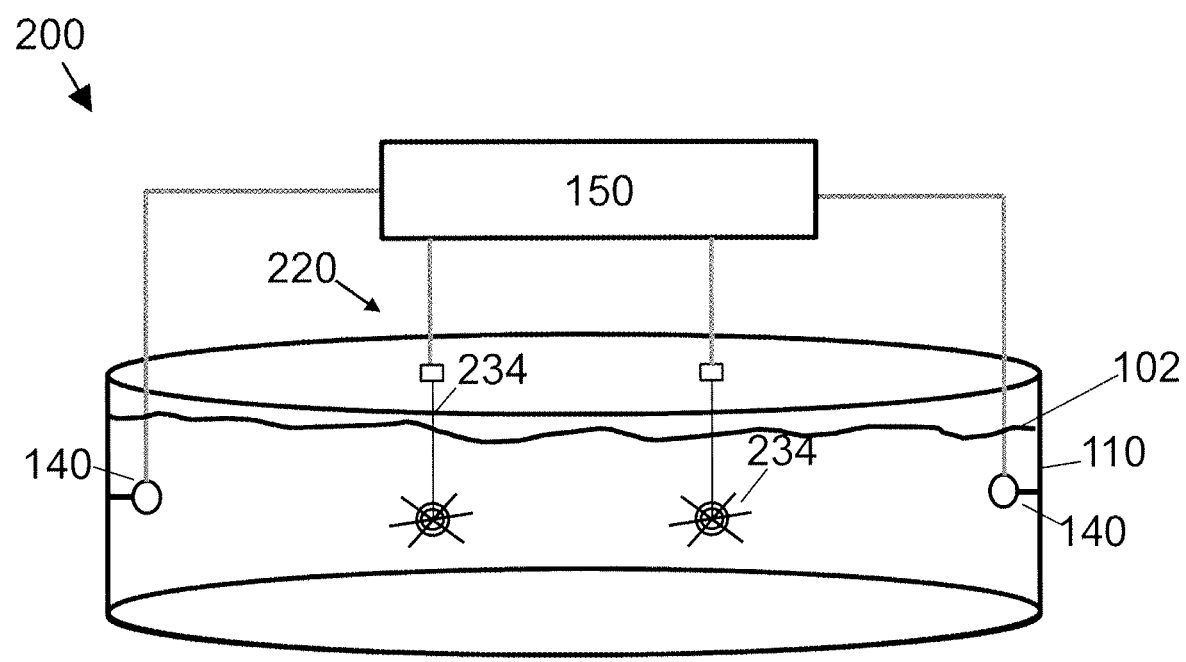
FIG. 2 is a schematic representation of a second example of a wastewater treatment system that includes a mechanical mixing system in accordance with one or more aspects of the invention.

A schematic of a wastewater treatment system according to another embodiment is shown generally at 200 in FIG. 2. The system 200 includes a vessel 110, a mixing system 220, at least one sensor 140, and a controller 150. The vessel 110, at least one sensor 140, and controller 150 may be characterized as previously described in reference to system 100 of FIG. 1. However, the mixing system 220 of system 200 is configured as a mechanical mixing system, which changes certain aspects of both function and control of the system. As used herein, the term "mechanical mixing" refers to movement under the influence of mechanical energy. Non-limiting examples of mechanical mixing devices includes propeller, turbine, and paddle mixers.

The mechanical mixing system 220 includes at least one motor driven mixing structure 234, and may also be referred to herein as a mechanical mixing structure. In some embodiments, the motor driven mixing structure 234 is one of an impeller, propeller, or a plunger type linear motion device. For example, a plunger type linear motion device may include mixing plates, blades, or a disk as a mixing mechanism that is attached to a plunger shaft, and linear motion of the shaft drives the mixing mechanism, which imparts a motive force in the fluid. One suitable example of a plunger type linear motion device is the Ovivo® Linear Motion Mixer (Canada). Non-limiting examples of impellers include radial flow and axial flow impellers. The motor driven mixing structures 234 are submerged in the wastewater 102 present in the vessel 110 and function to mix the wastewater 102. Multiple motor driven mixing structures 234 may be positioned within the vessel 110, and their positioning may depend on several factors, including the particular application and the size of the vessel. For instance, in smaller vessels, impeller-type motor driven mixing structures may be mounted off-center and/or at an angle. The motor driven mixing structures 234 may be powered by electric power, which as explained below, can be controlled by the controller 150.

Wastewater treatment system 200 also includes at least one sensor 140 that is configured to measure at least one property of the wastewater 102 as previously described. The at least one sensor 140 may be positioned within the vessel 110 at one or more locations, such as along a sidewall of the vessel.

Components of the mixing system 220, such as the motor driven mixing structure 234, may be controlled by the controller 150 based on measurements taken by the at least one sensor 140 in a similar manner as described above in reference to mixing system 120. For example, the controller 150 may initially activate the mixing system 220 (e.g., by controlling power to the motor driven mixing structure 234), and then use the at least one sensor 140 to obtain a first measured value at a first time for at least one property of the wastewater 110 present in the vessel 110. The controller 150 may then obtain a second measured value at a second time for the at least one property of the wastewater, calculate a difference between the first and second measured values, perform a comparison between the difference and a predetermined threshold or predetermined allowable range of differences, and responsive to a result of the comparison, control a component of the mixing system 220, which in this instance is the motor driven mixing structures 234. In a similar manner as described above in reference to the motor driven pump 124, power to the motor driven mixing structure 234 may be terminated, maintained, or modulated (in instances where the motor driven mixing structure is outfitted with a VSD or VFD) by the controller 150 based on the comparison result.

In some embodiments, the controller 150 may use successive measurements from a sensor 140 at one location of the vessel 110 and perform a localized control of one or more mechanical mixing structure 234 in the vicinity of the sensor 140. For instance, if successive measurements from one sensor indicate a "dead" zone in a portion of the vessel 110, then power to one or more motor driven mixing structure 234 near the dead zone can be increased or maintained to cause further mixing of the wastewater in this area of the vessel 110. Meanwhile, if measurements from sensors located in other portions of the vessel 110 indicate that there is adequate mixing, then the controller 150 may terminate or decrease power to mechanical mixing structures 234 positioned near those areas, which may result in overall decreased energy consumption by the mixing system 220.

Figure 3:
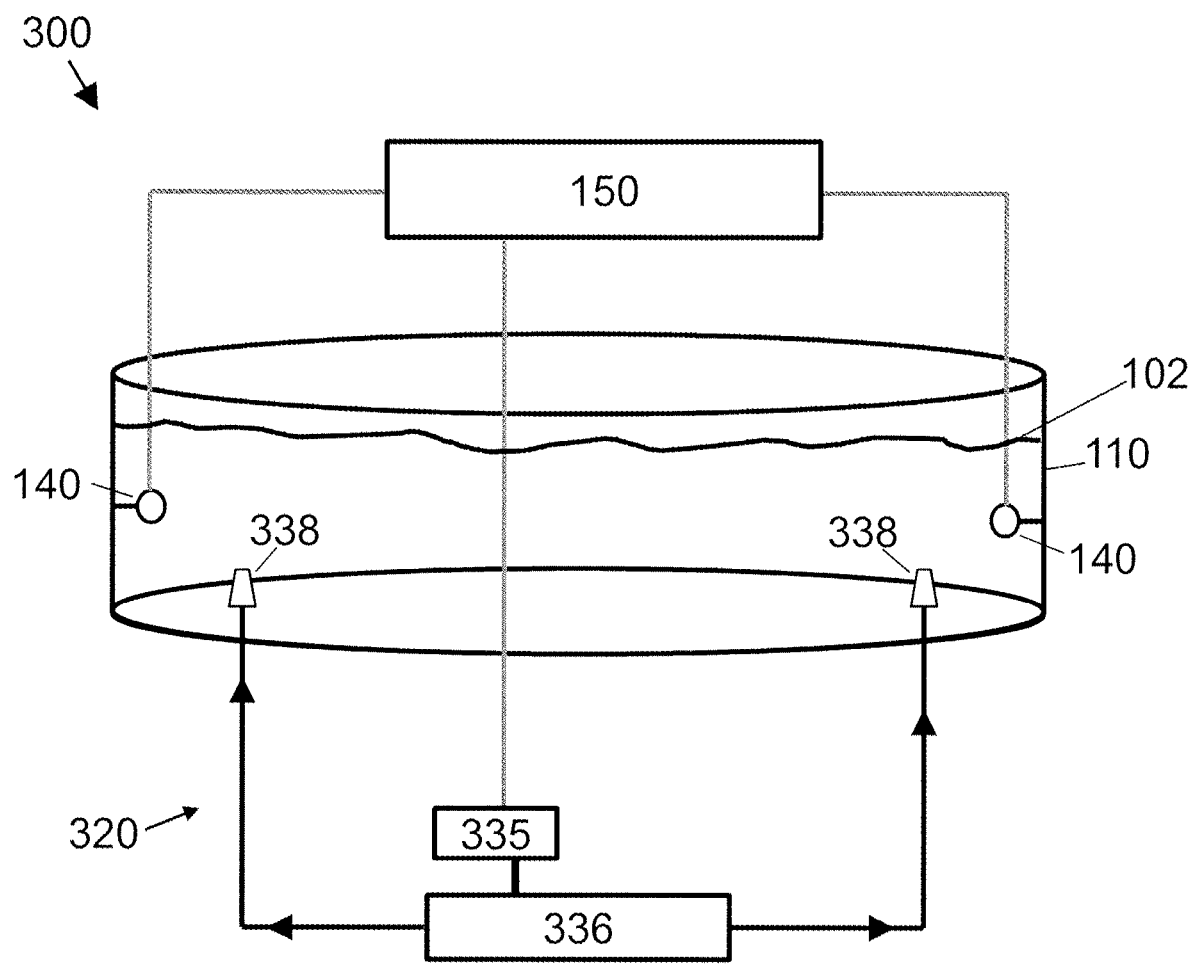
FIG. 3 is a schematic representation of a third example of a wastewater treatment system that includes a pneumatic mixing system in accordance with one or more aspects of the invention.

A schematic of a wastewater treatment system according to yet another embodiment is shown generally at 300 in FIG. 3. The system 300 includes a vessel 110, a mixing system 320, at least one sensor 140, and a controller 150. The vessel 110, at least one sensor 140, and controller 150 may be characterized as previously described. However, the mixing system 320 of system 300 is configured as a pneumatic mixing system. As used herein, the term "pneumatic mixing" refers to movement under the influence of gas flow. For example, according to one embodiment, the pneumatic mixing system is actuated using compressed air, nitrogen, or biogas as a driving force. Air diffusers are one example of a pneumatic mixing device.

The pneumatic mixing system 320 includes a fluid control device 335, a source of pressurized gas 336, and at least one diffuser nozzle 338. The fluid control device 335 is fluidly coupled to a source of pressurized gas 336, and functions to control the amount of pressurized gas that is introduced to the at least one diffuser nozzle 338. According to certain embodiments, the fluid control device 335 is one of a valve and a motor driven pump. The source of pressurized gas 336 may be air, nitrogen, biogas, or any other type of gas suitable for a particular mixing application. The at least one diffuser nozzle 338 is fluidly connected or connectable to the source of pressurized gas 336 and is positioned at one or more locations within the vessel 110. During mixing operations, the diffuser nozzles 338 are submerged in wastewater 102 present in the vessel 110, and introduce pressurized gas to the wastewater to create a mixing effect. According to certain embodiments, the diffuser nozzles 338 may be positioned in proximity to the bottom or floor of the vessel 110.

At least one sensor 140 is also included in wastewater treatment system 300 and according to some embodiments positioned within the vessel 110 at one or more locations, such as at a sidewall or center region of the vessel. The at least one sensor 140 is in fluid communication with the wastewater 102 present within the vessel 110 and is configured to measure at least one property of the wastewater 102 as previously described.

One or more components of the mixing system 320 may be controlled by the controller 150 based on measurements taken by the at least one sensor 140 in a similar manner as described above. For example, responsive to a result of the comparison between the successive measurements taken by the at least one sensor 140, the controller 150 may control the fluid control device 335. If the fluid control device 335 is a valve, then the controller 150 may actuate or otherwise control the opening and closing of the valve. For instance, if the difference between the first and second measured property values exceeds the predetermined threshold, then the controller 150 can maintain the setting of the valve or can increase the valve opening so that it provides more gas to the diffuser nozzles, which creates a greater mixing effect within the vessel 110. Likewise, if the difference between the first and second measured property values meets or is within the predetermined threshold, then the controller 150 can close the valve, which terminates gas flow to the vessel 110. In another example, if the fluid control device 335 includes a motor, power to the motor may be controlled by the controller 150 in a similar manner as described above.

Figure 4:
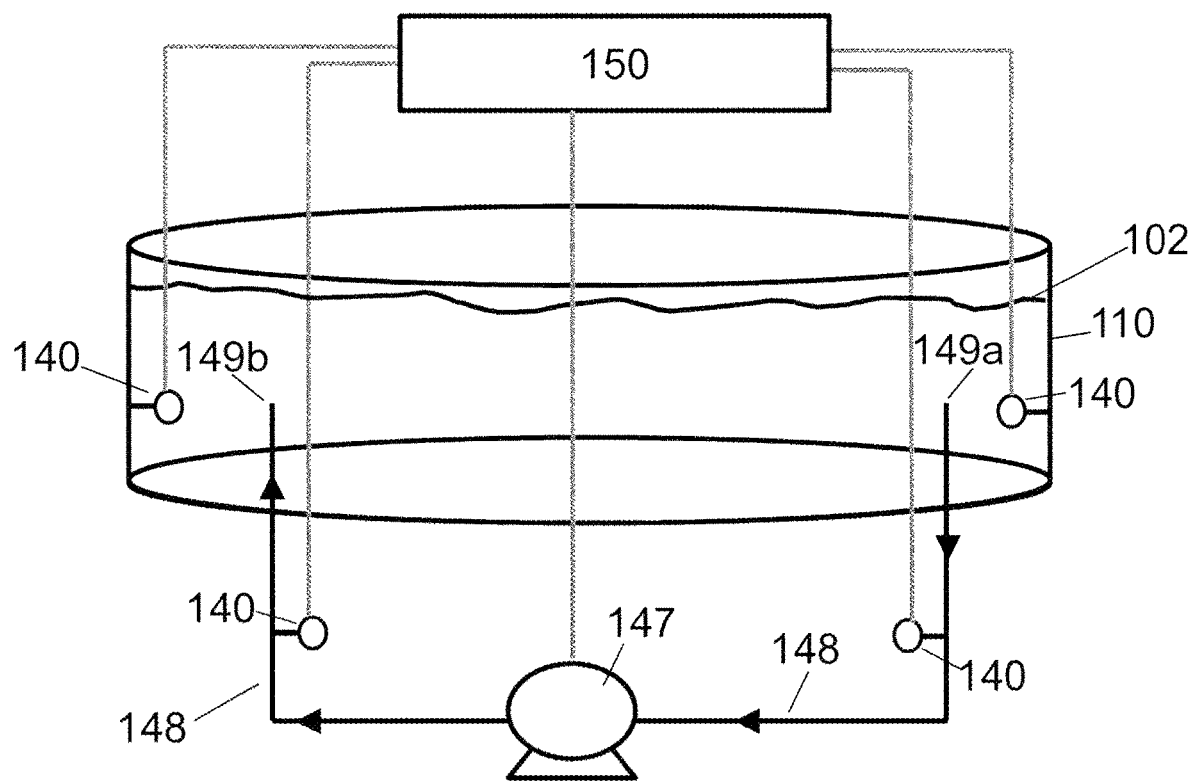
FIG. 4 is a schematic representation of an alternative example of a wastewater treatment system in accordance with one or more aspects of the invention.

FIG. 4 shows a schematic of an alternative embodiment where a sample loop 148 is used to measure wastewater 102 in the vessel 110. The sample loop 148 may be used with any of wastewater treatment systems 100, 200, or 300 and may function to provide measurements to the controller 150 for purposes of controlling one or more components of the mixing system 120, 220, 320. A portion of the sample loop 148 is positioned external to the vessel 110 and is fluidly connected or connectable to the internal volume of the vessel. The sample loop 148 is configured to withdraw wastewater 102 from the vessel 110 and to re-introduce the wastewater into the vessel 110. The example embodiment shown in FIG. 4 includes a pump 147 that is positioned in the sample loop 148 and is configured to pump wastewater 102 from an inlet 149*a* to an outlet 149*b* of the sample loop 148. The inlet 149*a* and outlet 149*b* of the sample loop 148 are in fluid communication with wastewater 102 present in the vessel 110. At least one sensor 140 is positioned on the sample loop 148. The at least one sensor 140 may be positioned on the suction side and/or discharge side of the pump 147. At least one sensor 140 is also positioned within an internal volume of the vessel 110.

The sensors 140 are operatively coupled to the controller 150 as previously described, and according to certain embodiments, the pump 147 may be operatively coupled to and controlled by the controller 150. For instance, the pump 147 may be activated at predetermined times or time intervals to pump wastewater 102 from the vessel 110 into the sample loop, and at least one sensor 140, also controlled by the controller 150, takes measurements as described above in reference to wastewater treatment system 100 of FIG. 1.

The sample loop 148 also allows for one or more sensors to be positioned external to the vessel 110, which allows them to be more accessible for installation, maintenance, and repair purposes. Thus, according to some embodiments, the system 200 of FIG. 2 and the system 300 of FIG. 3 may implement the sample loop 148 instead of or in addition to having the sensors 140 positioned within the vessel 110.

Figure 9:
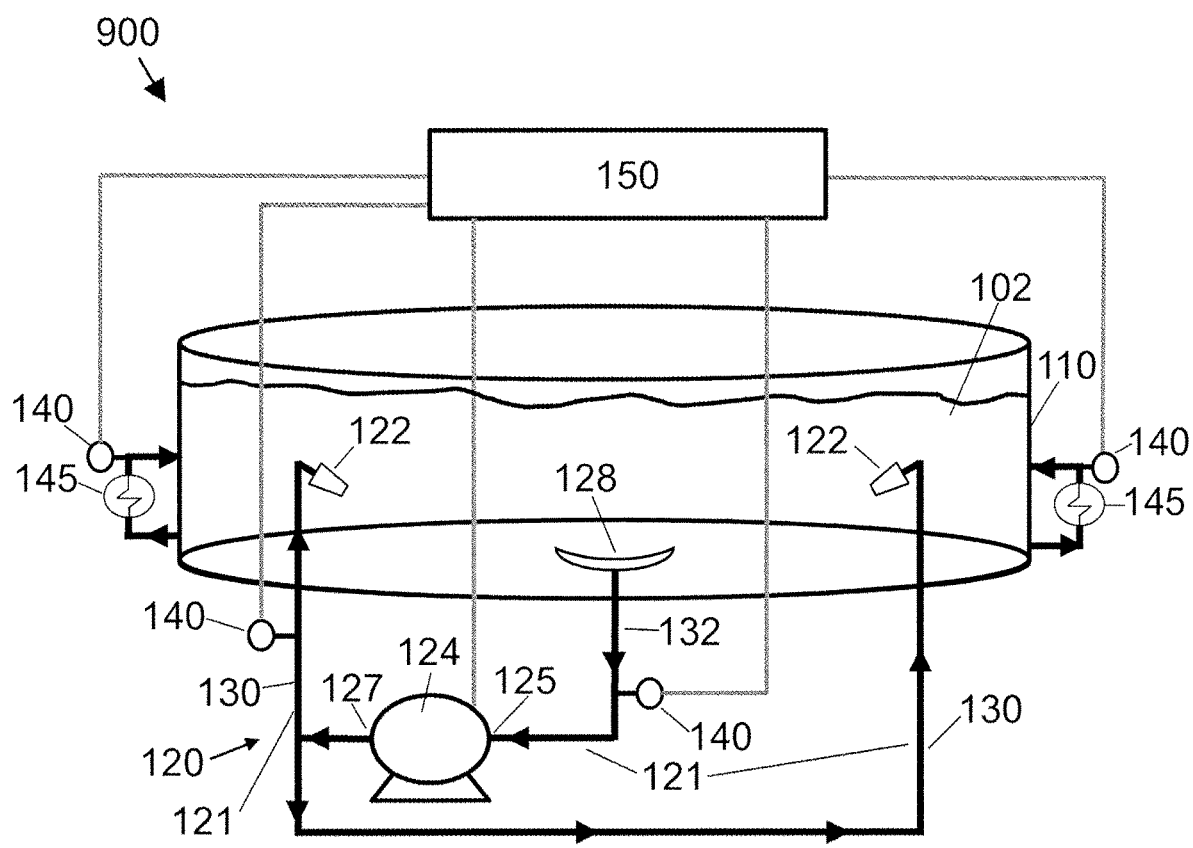
FIG. 9 is a schematic representation of a wastewater treatment system used in performing a test in accordance with one or more aspects of the invention.

According to some embodiments, a heater, such as a heat exchanger, may be integrated with the sample loop 148, or may be integrated as a separate heating loop. An example of a heater 145 is shown in FIG. 9, which is used in the Example discussed below. The heater may function to heat wastewater 102 removed from the vessel 110, which can then be re-introduced to the vessel 110 and mixed with other wastewater 102 present in the vessel 110. The heater may be controlled by the controller 150 and implemented with the use of a pump that pumps wastewater through the heater. The controller 150 may control the heater to heat wastewater at predetermined intervals, or to heat the wastewater in the vessel to a predetermined temperature, thereby allowing the heater to operate until the desired temperature is achieved. A heater may be desired for certain types of applications, such as during digestion operations.

EXAMPLES

The function and advantage of these and other embodiments of the systems and techniques disclosed herein will be more fully understood from the example below. The following example is intended to illustrate the benefits of the disclosed treatment approach, but does not exemplify the full scope thereof.

A wastewater treatment system having a vessel configured as an anaerobic digester and implemented with a Jetmix™ vortex hydraulic mixing system (Evoqua Water Technologies LLC (Warrendale, Pa.)) was used for testing and comparing power consumption using the optimized control scheme described herein against a conventional control scheme where the mixing pump was operated on a continuous basis. FIG. 9 is a schematic of an example of the wastewater treatment system 900 used during the testing, and includes a heating loop with a heat exchanger 145. Although not explicitly shown in FIG. 9, the heating loop may also include a pump that functions to transfer wastewater from the vessel through the heating loop. Sensors 140 were positioned on each of the two heating loops, as shown in FIG. 9, as well as along the recirculation loop that includes the motor driven pump 124 (e.g., sensor 140 positioned at one or both of the supply conduit 130 and the return conduit 132), for measuring properties of the wastewater 102. The mixing pump was operated at 80% VFD for the test using the conventional control scheme, and was operated at 100% for the test using the optimized control scheme.

The nozzles 122 used in the hydraulic mixing system were ASTM A532 class II, Type C Chrome iron with a minimum hardness of 450/550 Brinell throughout the entire nozzle wall. The nozzle wall was ½" thick with the same hardness is found throughout the nozzle wall.

The optimized control scheme was executed by programming the controller 150 to operate the motor driven pump 124 for 5 minutes every hour. Temperature measurements of the wastewater 102 were taken by sensors 140 positioned in the vessel 110 and compared to measurements taken by the sensor 140 positioned along the recirculation loop 121. If the difference between the values measured within the vessel and external to the vessel was within the predetermined threshold (set at ±2° F.), then the mixing pump was deactivated at the end of the 5 minute period of time. If the difference between the values measured within the vessel and external to the vessel exceeded the predetermined threshold, then power to the mixing pump was maintained and it continued to operate beyond the 5 minute period of time. The sensors 140 were controlled to measure on a continuous basis, and the mixing pump continued to operate until each of the comparison values between measurements made within the vessel and external to the vessel were within the predetermined threshold. This ensured that the wastewater within the vessel was adequately mixed at all locations of the sensors positioned within the vessel.

Figure 6:
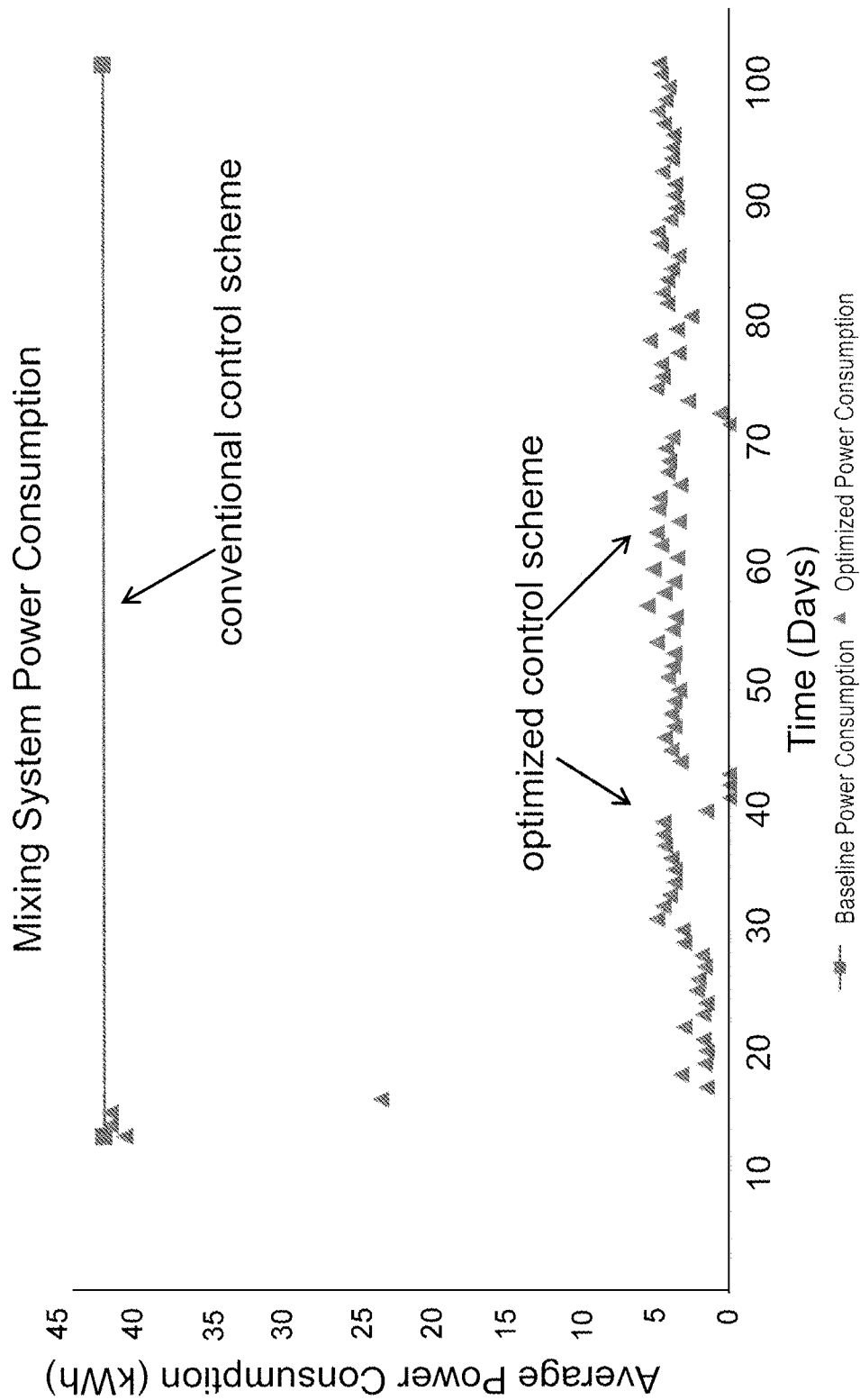
FIG. 6 is a graph of power consumption of a mixing system according to an aspect of the invention.

FIG. 6 is a graph of average power consumption of the hydraulic mixing system using both control schemes over an approximate 12-week time interval. The results indicate that the mixing system used significantly less energy over the time period when operating using the optimized control scheme as compared to the conventional control scheme. The average power consumption using the optimized control scheme was less than about 5 kWh, whereas the average power consumption using the conventional control scheme was about 43 kWh. The energy consumption was thus decreased by about 8-fold.

Figure 7:
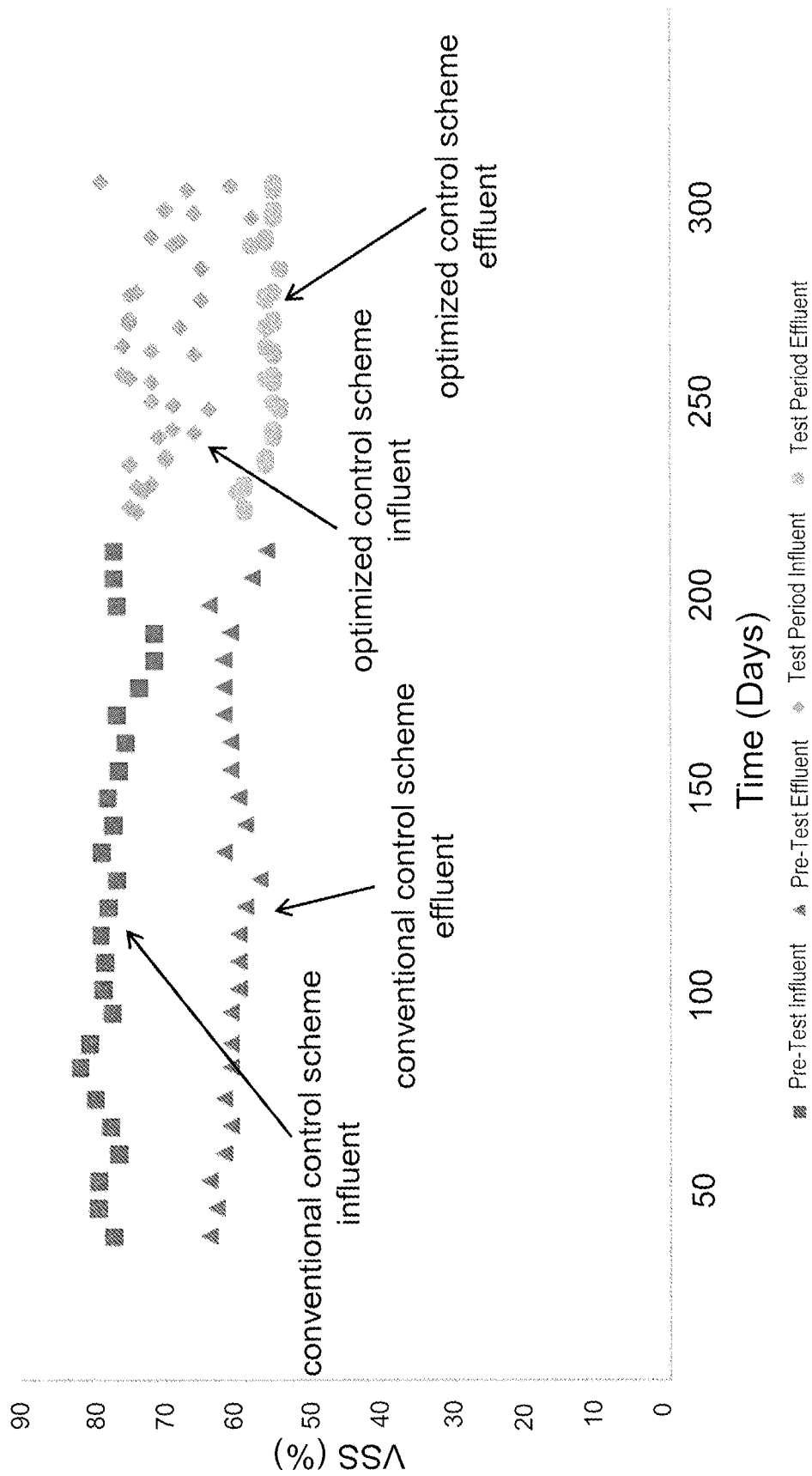
FIG. 7 is a graph of digester performance according to an aspect of the invention.

FIG. 7 is a graph of digester performance measured over a time period spanning an approximate 6-month period prior to the testing period (using the conventional control scheme) through the approximate 12-week testing period that utilized the optimized control scheme. VSS measurements were taken of both the influent and effluent of the vessel and are plotted in FIG. 7. The results indicate that the digester performance was maintained using the optimized control scheme. The influent and effluent VSS values did not change significantly during the testing period.

Figure 8:
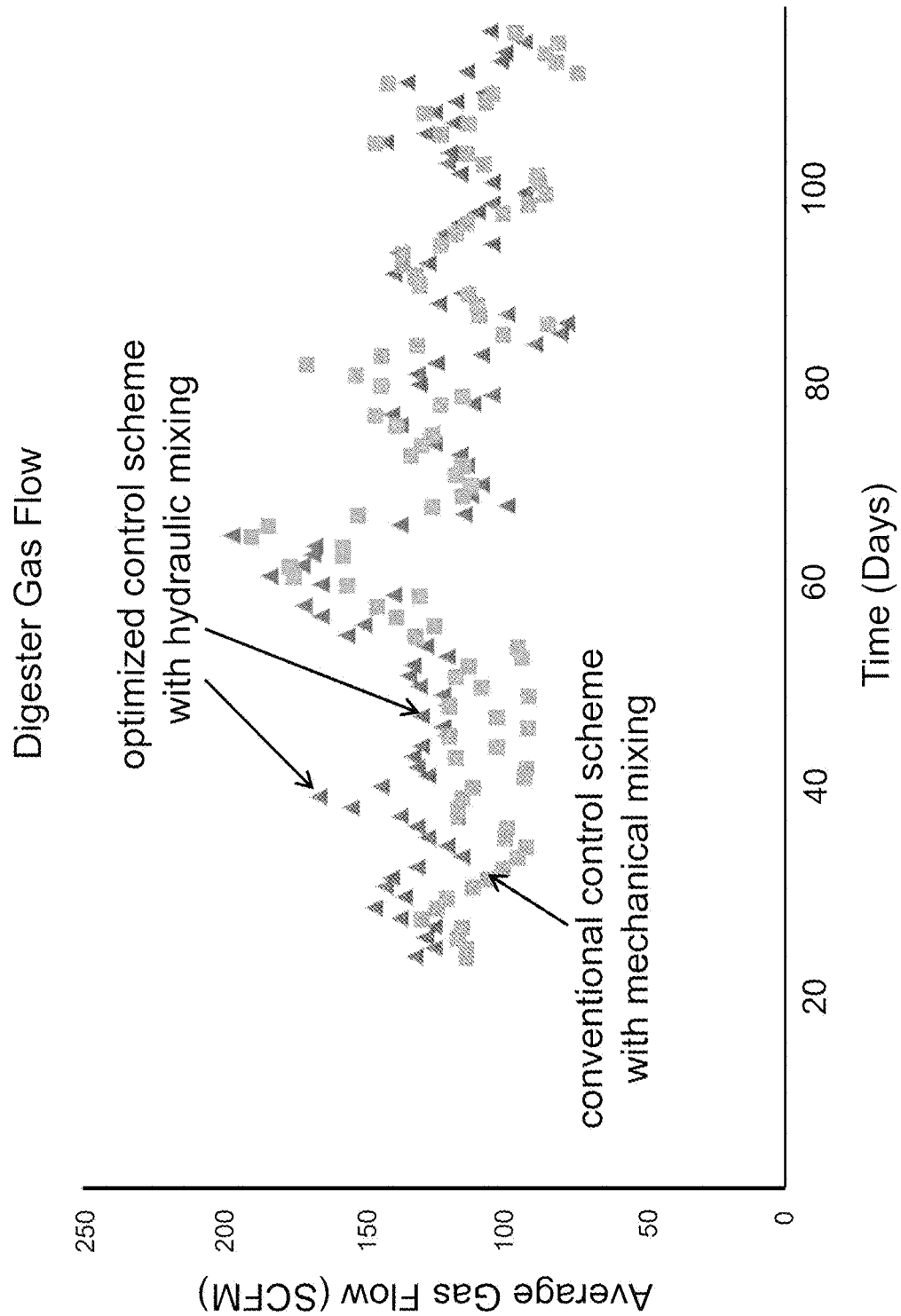
FIG. 8 is a graph of average digester gas flow rate according to an aspect of the invention.

FIG. 8 is a graph of average digester gas flow rate (i.e., biogas production) measured during the testing period (i.e., the same 12-week time interval as in FIG. 6) for the wastewater treatment system 900 as shown in FIG. 9 configured with the hydraulic mixing system and using the optimized control scheme. Also plotted in FIG. 8 is the biogas production for a wastewater treatment system having the same wastewater composition as that of the system 900, but instead using a mechanical mixing system and the conventional control scheme. The results indicate that the average biogas production for both systems was about the same, indicating that biogas production is not compromised when using the optimized control scheme.

The results from the experiment indicated that substantial energy savings can be achieved using the control logic associated with the disclosed invention without sacrificing significant process performance, such as biogas production and VSS parameters.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls.

Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A method for treating wastewater, the method comprising:
    activating a mixing system that imparts a motive force on wastewater in a vessel for a first time interval;
    measuring at least one property of a first portion of the wastewater at a first time within the first time interval while the first portion of the wastewater is inside the vessel;
    deactivating the mixing system at an end of the first time interval;
    reactivating the mixing system for a second time interval subsequent to deactivating the mixing system at the end of the first time interval;
    removing a second portion of the wastewater from the vessel;
    measuring the at least one property of the second portion of the wastewater at a second time within the second time interval while the second portion of the wastewater is outside the vessel;
    calculating a difference between the at least one property measured at the first time and the at least one property measured at the second time;
    determining whether the difference is within a predetermined allowable range of differences defined by an upper limit and a lower limit; and
    responsive to the difference being within the predetermined allowable range of differences, deactivating a component of the mixing system.

2. The method of claim 1, further comprising, responsive to the difference being outside the predetermined allowable range of differences, one of modulating or maintaining power supplied to the component.

3. The method of claim 1, wherein removing the second portion of the wastewater from the vessel includes introducing the second portion of the wastewater into a recirculation loop fluidly connected between an outlet of the vessel and an inlet of the vessel.

4. The method of claim 1, further comprising re-introducing the second portion of the wastewater to the vessel after measuring the at least one property of the second portion of the wastewater.

5. The method of claim 1, wherein measuring the at least one property of the first portion of the wastewater includes measuring a property selected from the group consisting of temperature, pH, total suspended solids (TSS), dissolved oxygen (DO), and oxidation reduction potential (ORP).

6. The method of claim 1, wherein the deactivating of the component of the mixing system responsive to the difference being within the predetermined allowable range of differences reduces power consumption by at least 50%.

7. A method for treating wastewater, the method comprising:
    activating a mixing system comprising a plurality of independent components that impart a motive force on wastewater in a vessel for a first time interval;
    measuring at least one property of a first portion of the wastewater at a first time within the first time interval;
    deactivating the mixing system at an end of the first time interval;
    reactivating the mixing system for a second time interval subsequent to deactivating the mixing system at the end of the first time interval;
    measuring the at least one property of a second portion of the wastewater at a second time within the second time interval;
    calculating a difference between the at least one property measured at the first time and the at least one property measured at the second time;
    determining whether the difference is within a predetermined allowable range of differences; and
    responsive to the difference being within the predetermined allowable range of differences, controlling a subset of the plurality of independent components of the mixing system to provide mixing in a localized portion of the vessel containing the subset of the plurality of independent components of the mixing system.

8. The method of claim 7, wherein controlling the subset of the plurality of independent components includes one of modulating or maintaining power supplied to the subset of the plurality of independent components responsive to the difference being outside the predetermined allowable range of differences.

9. The method of claim 7, further comprising:
    measuring the at least one property of the first portion of the wastewater while the first portion of the wastewater is inside the vessel;
    removing the second portion of the wastewater from the vessel; and
    measuring the at least one property of the second portion of the wastewater while the second portion of the wastewater is outside the vessel.

10. The method of claim 9, wherein removing the second portion of the wastewater from the vessel includes introducing the second portion of the wastewater into a recirculation loop fluidly connected between an outlet of the vessel and an inlet of the vessel.

11. The method of claim 9, further comprising re-introducing the second portion of the wastewater to the vessel after measuring the at least one property of the second portion of the wastewater.

12. The method of claim 7, wherein measuring the at least one property of the first portion of the wastewater includes measuring a property selected from the group consisting of temperature, pH, total suspended solids (TSS), dissolved oxygen (DO), and oxidation reduction potential (ORP).

* * * * *